United States Patent [19]

DeDecker et al.

[11] Patent Number: 5,904,666
[45] Date of Patent: May 18, 1999

[54] METHOD AND APPARATUS FOR MEASURING FLOW RATE AND CONTROLLING DELIVERED VOLUME OF FLUID THROUGH A VALVE APERTURE

[75] Inventors: Paul G. DeDecker, Warren; Paul S. Freed, Bloomfield Hills, both of Mich.

[73] Assignee: L.VAD Technology, Inc., Detroit, Mich.

[21] Appl. No.: 08/912,419

[22] Filed: Aug. 18, 1997

[51] Int. Cl.[6] .................................................. A61M 5/00
[52] U.S. Cl. .............................. 604/65; 604/49; 604/131
[58] Field of Search ............................... 604/65–67, 131, 604/49, 50, 30, 31, 132, 133, 151–153; 128/DIG. 13

[56] References Cited

U.S. PATENT DOCUMENTS

| | | |
|---|---|---|
| 3,553,736 | 1/1971 | Kantrowitz et al. . |
| 3,585,983 | 6/1971 | Kantrowitz et al. . |
| 4,004,298 | 1/1977 | Freed . |
| 4,051,840 | 10/1977 | Kantrowitz et al. . |
| 4,092,742 | 6/1978 | Kantrowitz et al. . |
| 4,630,597 | 12/1986 | Kantrowitz et al. . |
| 4,634,422 | 1/1987 | Kantrowitz et al. . |
| 4,692,148 | 9/1987 | Kantrowitz et al. . |
| 4,733,652 | 3/1988 | Kantrowitz et al. . |
| 4,809,681 | 3/1989 | Kantrowitz et al. . |
| 4,810,246 | 3/1989 | Frisch et al. . |
| 4,913,700 | 4/1990 | Kantrowitz et al. . |
| 5,139,508 | 8/1992 | Kantrowitz et al. . |
| 5,169,379 | 12/1992 | Freed et al. . |
| 5,242,415 | 9/1993 | Kantrowitz et al. . |
| 5,336,167 | 8/1994 | Sullivan et al. ....................... 604/65 X |
| 5,356,378 | 10/1994 | Doan ......................................... 604/65 |
| 5,372,709 | 12/1994 | Hood ..................................... 604/65 X |
| 5,423,746 | 6/1995 | Burkett et al. ....................... 604/131 X |
| 5,445,622 | 8/1995 | Brown . |
| 5,482,446 | 1/1996 | Williamson et al. . |

FOREIGN PATENT DOCUMENTS 402872  12/1990  European Pat. Off. .

OTHER PUBLICATIONS

International Search Report, Jul. 17, 1998 for International Application No. PCT/US97/24041.

*Primary Examiner*—John D. Yasko
*Attorney, Agent, or Firm*—Young & Basile, P.C.

[57] ABSTRACT

An apparatus for measuring flow rate and controlling delivered volume of fluid flow in a fluid conduit is disclosed including a valve having a fixed aperture disposed in the fluid conduit for selectively opening and closing the aperture between an open position and a closed position. The valve is selectively closed when a predetermined volume has passed through the valve. Differential pressure is measured across the valve and the differential pressure is accumulated with respect to time to provide a value corresponding to volume of fluid flow passing through the valve when in the open position. A method for measuring flow rate and controlling delivered volume of fluid flow through a fluid conduit includes the steps of selectively opening and closing a valve having a fixed aperture disposed in the fluid conduit between an open position and a closed position, measuring a differential pressure between a first pressure on an upstream side of the valve and a second pressure on a downstream side of the valve, and when the valve is in the open position, accumulating the differential pressure with respect to time to obtain a value corresponding to volume of fluid flow passing through the valve.

16 Claims, 3 Drawing Sheets

METHOD AND APPARATUS FOR MEASURING FLOW RATE AND CONTROLLING DELIVERED VOLUME OF FLUID THROUGH A VALVE APERTURE

FIELD OF THE INVENTION

The present invention relates to a method and apparatus for measuring flow rate and controlling volume of fluid passing through a valve aperture by measuring the differential pressure between an upstream location and a downstream location with respect to the valve aperture and determining the volume of fluid passing through the valve aperture by accumulating the differential pressure measurements over time, and closing the valve to terminate flow when a predetermined value corresponding to volume is reached.

BACKGROUND OF THE INVENTION

In the past, when values for the flow rate and volume passing through a pipeline or other fluid conduit have been desired, a metering orifice is normally installed and the pressure difference measured in order to determine the flow rate through the metering orifice. The addition of a metering orifice increases the pressure required to overcome the line losses through the pipeline, and is particularly undesirable in situations where the additional size, weight and/or pressure loss are of particular importance. The addition of a valve is necessary to control the repetitive injection or transfer of a fixed volume through the pipeline adding weight, cost and line losses to the system.

SUMMARY OF THE INVENTION

The present invention seeks to overcome the drawbacks and disadvantages of the prior known metering orifices. While the present invention is particularly well adapted for the controller/actuator of a diastolic augmentation system, it is believed to have much broader application and use, extending virtually to any piping fluid system conveying gas or liquids through a pipeline having a valve disposed in the pipeline along the fluid path for injection of fixed volumes of fluids respectively. Heretofore, it has not been appreciated that the valve opening can be used as a metering orifice or restriction, allowing pressure measurements to be taken upstream of the valve and downstream of the valve, and the differential pressure to be used to determine the flow rate, and by accumulating the differential pressure measurements over time to be used to determine the volume that passes through the valve orifice.

By way of example, and not limitation, an inflate valve of a mechanical auxiliary ventricle system has a differential pressure sensor mounted across the valve. During inflation, the valve functions as an orifice, and the pressure drop across the valve is proportional to the air flow velocity entering the blood pump. The integral of the pressure drop, therefore, is proportional to the volume of gas in the blood pump. Theoretically, a program according to the present invention computes the value of the integral after each data acquisition cycle (typically 4 milliseconds (ms)) and compares the calculated value to the target inflation volume. When the target inflation volume is reached, inflation is deemed complete and the inflate valve is closed. Actually, it has been found that accumulating differential pressure measurements ($\Delta P$) over time and comparing the accumulated $\Delta P$ to a predetermined value, that takes into consideration all of the constant values, conversion factors and the like, provides a determination of whether the desired volume of fluid has passed through the valve orifice. The target inflation volume is physician adjustable from 25% to 110% of nominal stroke volume (50 cubic centimeters (cc)). In addition to reaching the target inflation volume, there are also several redundant safety controls which terminate inflation to prevent blood pump over-inflation: namely, if the current value of inflation time duration is longer than the inflation time safety limit; if the pressure in the drive line is higher than the inflation pressure safety limit; or if the differential pressure (pressure across the inflate valve) is close to zero, indicating that airflow has virtually stopped.

In its broadest sense, the present invention provides an apparatus for measuring as well as controlling fluid flow through a valve movable between an open position and a closed position. The apparatus includes means for measuring a differential pressure between a first pressure on an upstream side of the valve and a second pressure on a downstream side of the valve, and means for accumulating the differential pressure over time to obtain a value corresponding to a volume of fluid flow passing through the valve when in the open position. Further, the present invention provides a method for measuring fluid flow through a valve movable between an open position and a closed position to control fluid flow through a fixed valve aperture including the steps of measuring a differential pressure between a first pressure on an upstream side of the valve and a second pressure on a downstream side of the valve, and accumulating the differential pressure over time to obtain a value corresponding to a volume of fluid flow passing through the valve when in the open position.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
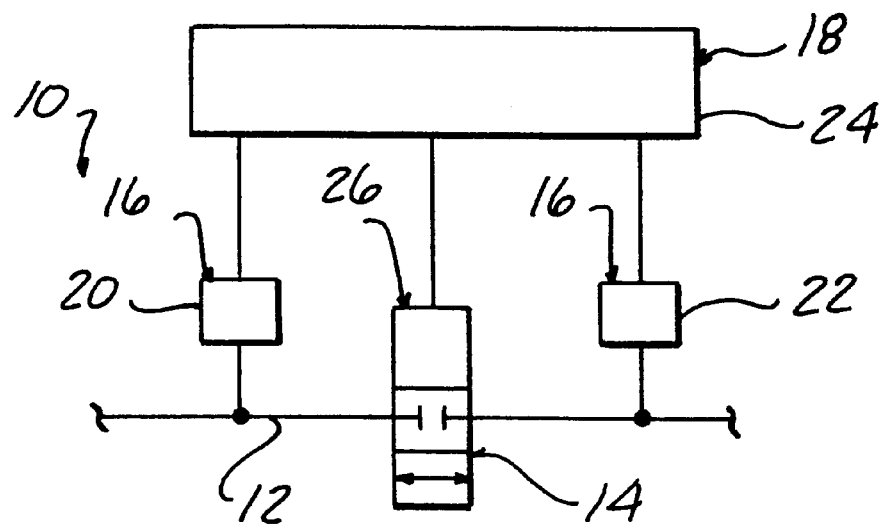
FIG. 1 is a simplified schematic view of an apparatus for measuring flow rate and controlling delivered volume of fluid flow through a valve aperture according to the present invention.

Referring now to FIG. 1, an apparatus 10 for measuring flow rate and controlling delivered volume of fluid flow through a fluid conduit 12 is illustrated. Valve means 14 is disposed in the fluid conduit 12 for selectively operating a fixed aperture between an open position and closed position. Measuring means 16 is provided for measuring a differential pressure between a first pressure on an upstream side of the valve means 14 and a second pressure on a downstream side of the valve means 14. Accumulating means 18 is also provided for accumulating the differential pressure with respect to time to determine a value corresponding to volume of fluid flow passing through the valve 14 when in the open position.

The differential pressure measuring means 16 can include first means 20 for measuring the first pressure on the upstream side of the valve means 14. The measuring means 16 can also include second means 22 for measuring the second pressure on a downstream side of the valve means 14. The first means 20 also generates a first signal corresponding to the first pressure. The second means 22 generates a second signal corresponding to the second pressure. Means 24 is provided for determining the differential pressure from the first and second signals. It should be recognized that the present invention includes the possibility of a single means for measuring the differential pressure between a first position upstream of the valve means 14 and a second position downstream of the valve means 14 and for generating a signal corresponding to the measured differential pressure.

Means is also provided for comparing the volume determined by the accumulating means 18 to a target volume value. When the volume is at least as great as the target volume value, actuating means 26 moves the valve means 14 to the closed position to prevent additional fluid flow through the aperture of the valve means 14. When the target volume value is greater than the volume, the actuating means 26 leaves the valve means 14 in the open position to allow additional fluid flow through the aperture of the valve means 14.

The apparatus 10 according to the present invention can also include means for comparing the differential pressure to zero. When the differential pressure is approximately equal to zero, or sufficiently close to zero to indicate virtually no flow, actuating means 26 moves the valve means 14 to the closed position. This prevents over inflation due to increased error as a percentage of the flow rate at low flows. When the differential pressure is sufficiently greater than zero to indicate that fluid flow is still occurring through the aperture of the valve means 14, the actuating means 26 leaves the valve means 14 in the open position to allow additional fluid flow through the aperture of the valve means 14.

The apparatus 10 according to the present invention can also include means for comparing the second pressure or downstream pressure to a safety pressure limit value. When the second pressure is at least as great as the safety pressure limit value, the actuating means 26 moves the valve means 14 to the closed position to prevent additional fluid flow through the aperture of the valve means 14. When the safety pressure limit value is greater than the second pressure, the actuating means 26 leaves the valve means in the open position to allow additional fluid flow through the aperture of the valve means 14.

The apparatus 10 according to the present invention can also include means for measuring a flow duration time interval and means for comparing the flow duration time interval to a flow duration safety limit value. When the flow duration time interval is at least as great as the safety limit value, the actuating means 26 moves the valve means 14 to the closed position to prevent additional fluid flow through the aperture of the valve means 14. When the safety limit value is greater than the flow duration time interval, the actuating means 26 leaves the valve means 14 in the open position to allow additional fluid flow through the aperture of the valve means 14.

The present invention provides means for measuring flow rate and controlling delivered volume of fluid flow through the fluid conduit 12, where the measuring means includes the steps of measuring a differential pressure between a first pressure on an upstream side of the valve means 14 and a second pressure on a downstream side of the valve means 14, and accumulating the differential pressure with respect to time to obtain a value corresponding to volume of fluid flow passing through the valve means 14 when in the open position.

Figure 2:
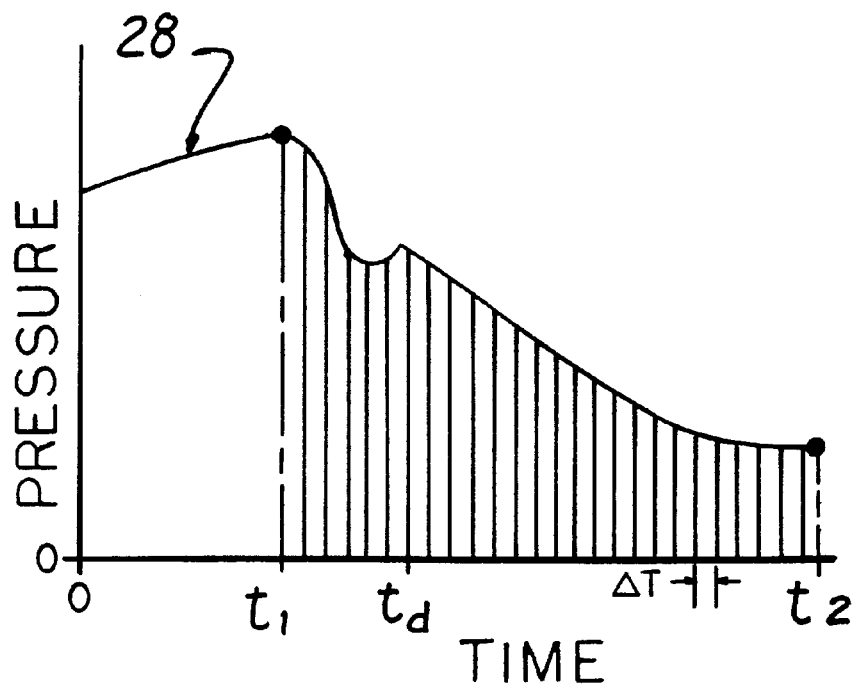
FIG. 2 is a graph showing differential pressure on the Y-axis and time on the X-axis where the area below the curve between a defined time period corresponds to a volume of fluid flow passing through the valve aperture when in an open position.

FIG. 2 is a graph showing differential pressure on the Y-axis versus time on the X-axis with a differential pressure curve 28 shown with respect to time according to the present invention. The differential pressure in the fluid conduit 12 increases slightly over time as illustrated between time zero and time $t_1$ until the pressure reaches a steady state, or until the valve means 14 is opened, such as at point $t_1$. When the valve means 14 is opened, a disturbance in the differential pressure curve between time mark $t_1$ and $t_d$ corresponds to the valve moving from the closed position to the fully opened position. The flow rate can not be accurately determined between time marks $t_1$ and $t_d$. This is considered an acceptable error if the time period between $t_1$ and $t_d$ is small in comparison to the time period $t_d$ and $t_2$. In theory, in order to determine the volume of fluid flow passing through the valve means 14 when in the open position, the differential pressure curve 28 is integrated with respect to time between the valve open time $t_1$ and the valve close time $t_2$. Since the differential pressure is sampled at 4 milliseconds intervals, in practice the measured differential pressure samples are accumulated in order to incrementally accumulate a value corresponding to a current volume of fluid flow that has passed through the valve means 14 when in the open position. The area under differential pressure curve 28 between times $t_1$ and $t_2$ corresponds to the volume of fluid flow passing through the valve means 14 when in the open position. It has been found that a target value corresponding to the desired volume and taking into account constant values, conversion factors and the like, can be calculated. This allows the differential pressure ($\Delta P$) to be accumulated over time and compared to this predetermined target value corresponding to the desired volume, to determine when the desired volume of fluid flow through the valve orifice has taken place. The operation of the apparatus for measuring flow rate and controlling delivered volume of fluid flow in a fluid conduit 12 according to the present invention will now be described in greater detail with respect to simplified schematic flow diagram illustrated in FIG. 3.

Figure 3:
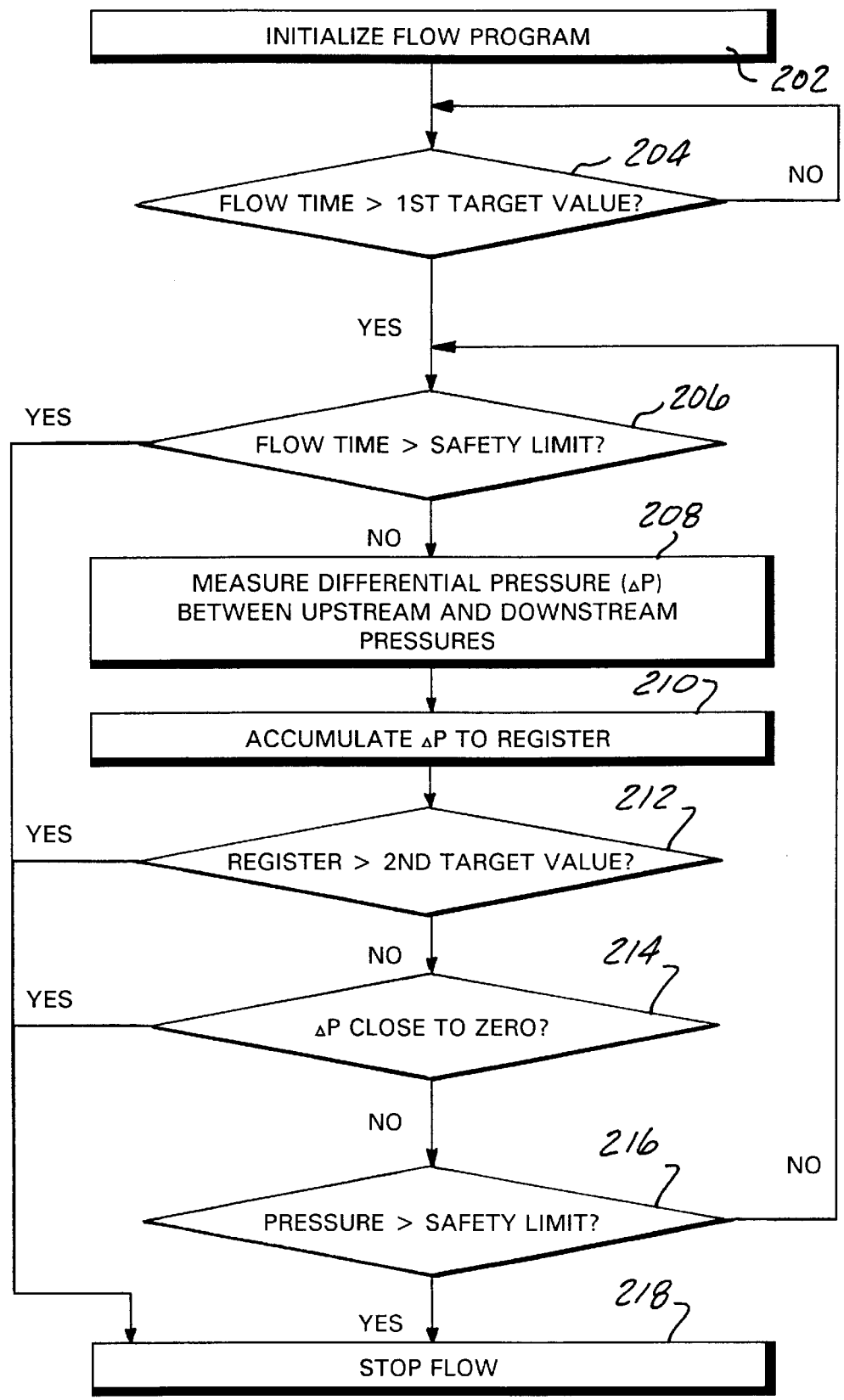
FIG. 3 is a simplified flow chart of a control program according to the present invention.

FIG. 3 is a simplified flow chart illustrating the operation of the program stored in memory of the control means. At the beginning of inflation all variables are initialized in step 202. It has been found to take approximately 28 milliseconds for the flow disturbance caused by the opening of the valve means 14 to subside and allow reliable pressure readings for flow determinations. Once the first target value corresponding to this predetermined time period has elapsed (step 204), a safety time limit is checked in step 206. If the elapsed flow time has exceeded a predetermined safety limit, valve means 14 is closed to prevent further fluid flow through the fluid conduit 12. Otherwise, the flow measurement routine (step 208, 210 and 212) commences to measure the differential pressure which corresponds to the volume of pressurized fluid passing through valve means 14. The simplified flow chart of FIG. 3, and in particular steps 208, 210 and 212 of the program of control means 40, measures the differential pressure with respect to time to determine a value corresponding to volume of fluid flow passing through the valve means 14 when in an open position. Valve means 14 is opened to begin fluid flow through the fluid conduit 12. During fluid flow, when valve means 14 is open, the aperture of the valve means 14 functions as a metering orifice. Step 208 measures a differential pressure measured between the pressure upstream of the valve means 14 and the pressure downstream of the valve means 14. The differential pressure (ΔP) is accumulated in a register at step 210. FIG. 2 illustrates a graph of differential pressure versus time, where the area under the curve corresponds to the volume of fluid flow through the aperture of the valve means 14. The register is evaluated to determine whether the accumulated ΔP corresponding to volume is greater than a predetermined second target value in step 212. If the register is not greater than the predetermined second target value corresponding to a predetermined volume, the routine continues to step 214. If the register is greater than the predetermined second target value, then the second target value has been reached and valve means 14 is moved to a closed position, thereby stopping flow at step 218. In step 214, the program compares the ΔP to zero to determine if there is sufficient pressure differential to continue fluid flow. If sufficient pressure differential exists to continue fluid flow through the valve orifice, the program continues to step 216. Otherwise, if the pressure differential is close to zero, the program stops flow in step 218. In step 216, the program compares the existing pressure to a safety limit. If the pressure is less than the safety limit, the program continues by returning to a position just before step 206. If the existing pressure is greater than the safety limit, the program stops flow by branching to step 218.

Figure 4:
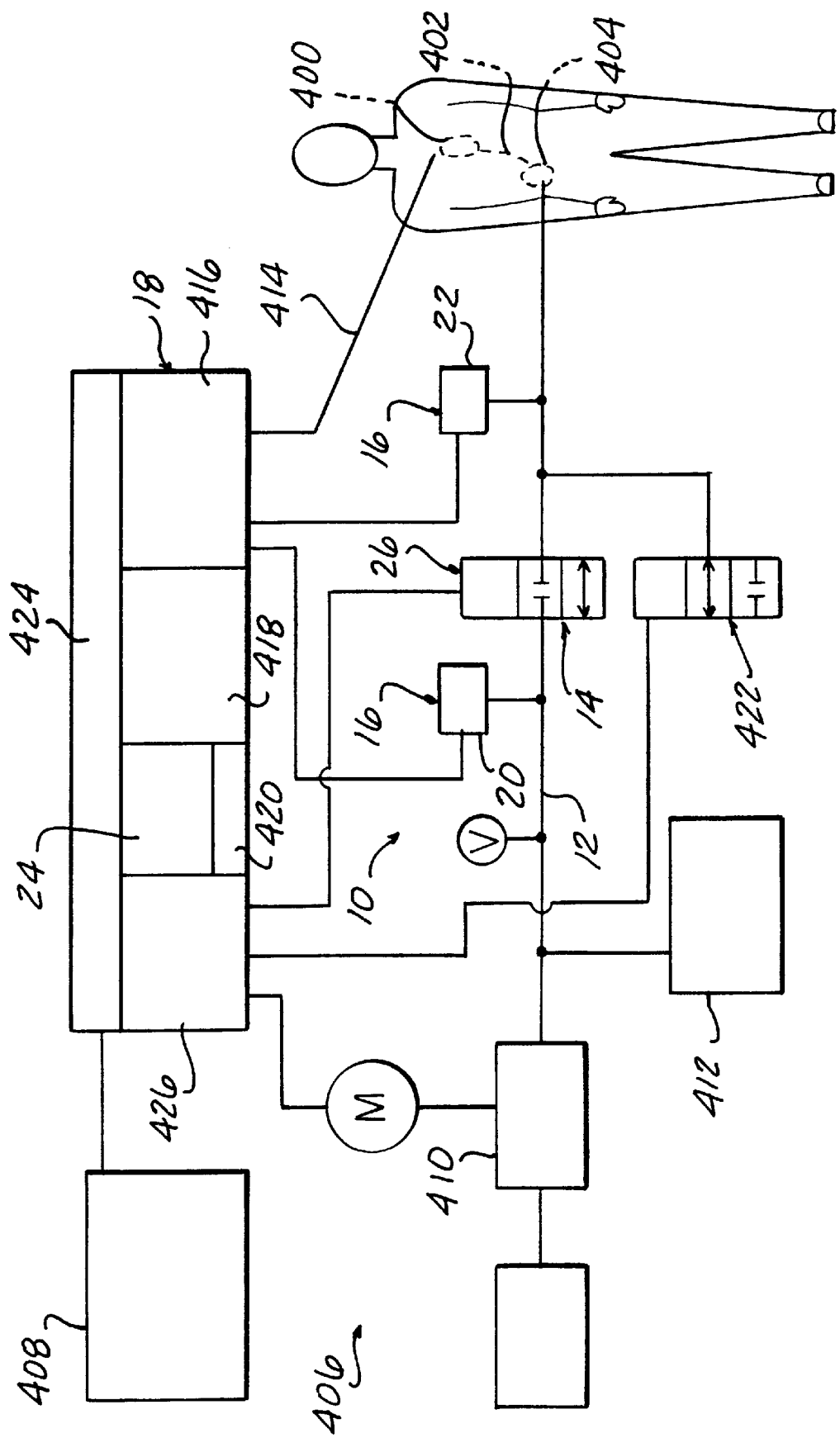
FIG. 4 is a simplified schematic view of an apparatus for measuring flow rate and controlling delivered volume of fluid flow through a valve aperture according to the present invention relating to diastolic augmentation.

By way of example and not limitation, the present invention will now be described in detail with respect to one possible application of the invention relating to diastolic augmentation as illustrated in FIG. 4. Diastolic augmentation is the physiologic concept of augmenting the work of the failing left ventricle, such as during chronic congestive left ventricular failure, by "adding" blood to the circulation during diastole and "removing" blood during the systole. This action provides external power to the circulatory system. Diastolic augmentation can be broken down into two major classes according to the intended duration of use: temporary pneumatic in-series left ventricular assist devices in use for a few hours to a few weeks; and permanent pneumatic in-series left ventricular assist devices in use for the remaining life of the patient.

The temporary version is more commonly known as an intra-aortic balloon pump. The intra-aortic balloon pump is a system for temporary left ventricular assistance which is used in-hospital for the treatment of acute congestive failure and other indications. The system has two main components: an inflatable balloon (usually 40 cubic centimeters (cc)) mounted on a catheter and inserted percutaneously, usually via the femoral artery, into the descending thoracic aorta. The balloon catheter is connected to a drive unit which includes pneumatic power (usually helium) and controls the timing of the inflation and deflation of the balloon.

The permanent version is referred to as a mechanical auxiliary ventricle or a dynamic aortic patch. The blood pump 400 for the mechanical auxiliary ventricle is an ellipsoidally shaped pumping bladder implanted into the wall of the descending thoracic aorta. The pumping bladder has no valves and only one moving part: a diaphragm which faces the lumen of the aorta and serves as the blood device interface. An air tube 402 emerges from the back of the device, leading to a percutaneous access 404 device. The blood pump 400 is constructed of an integrated bladder/blood interface made of polyurethane. The blood contacting surface is textured to enhance tissue adhesion and pseudo-neointima formation. The pump 400 also has refined geometry designed to reduce mechanical stresses. The percutaneous access device 404 serves as the conduit for pneumatic power and electrical signals to the mechanical auxiliary ventricle. The percutaneous access device 404 has a neck rising from a flange, and the external surface of the neck serves as the device-tissue seal. Examples of suitable percutaneous access devices and procedures are disclosed in U.S. Pat. No. 4,004,298; No. 4,634,422; No. 4,810,246; No. 4,913,700; No. 5,139,508; and No. 5,242,415 which are incorporated by reference herein.

The mechanical auxiliary ventricle system and the intra-aortic balloon pumps are considered in-series assist devices, because they are cardiac assist systems in which all the circulating blood passes through both the natural heart and the assist device. The drive unit 406 for the implanted mechanical auxiliary ventricle acts as both an actuator and a controller. The actuator-controller drive unit 406 has two configurations: a line-powered unit and a battery-powered unit. The drive unit 406 conveys pressurized air to power and to control the timing of inflation and deflation of the mechanical auxiliary ventricle blood pump 400. The line-powered drive unit serves as a power source and actuator/controller for the mechanical auxiliary ventricle when the patient is at a single location, such as the patient'home. The wearable drive unit is a battery-powered version of the drive unit and is intended to be worn by the mechanical auxiliary ventricle recipient on a belt or in a vest to allow the patient to be mobile.

In principle of operation and anatomic location, the mechanical auxiliary ventricle system closely resembles the intra-aortic balloon pump, which is designed for temporary circulatory support in a hospital setting. The relative location of both devices, in the descending thoracic aorta is similar (both are located below the carotid artery and above the diaphragm). The intra-aortic balloon pump is mounted on a catheter inserted into the lumen of the descending thoracic aorta, designed to be used for hours or days, after which the balloon pump catheter is removed from the body. The mechanical auxiliary ventricle system is surgically implanted in the wall of the descending thoracic aorta, and designed to remain in the body long-term. The stroke volume of the intra-aortic balloon pump is generally 35 to 40 cubic centimeters ($cm^3$ or cc); the stroke volume of the mechanical auxiliary ventricle blood pump is generally 55–60 cubic centimeters ($cm^3$ or cc).

The intra-aortic balloon pump is now a standard of care for numerous indications, including pump failure after acute myocardial infarction and cardiac surgery, and more recently, for unstable angina and support of high risk patients undergoing angioplasty. The hemodynamic efficacy of the intra-aortic balloon pump in acute left ventricular failure is well documented.

The mechanical auxiliary ventricle system operates in-series with the natural heart and is designed to augment left ventricular function either intermittently or continuously. When deactivated by choice of the patient, or for any other reason, the auxiliary ventricle deflates so that its diaphragm approximates the native aortic wall; the external portion of the percutaneous access device 404 can be detached, leaving the recipient unconnected to any external equipment. To reactivate the auxiliary ventricle, the external portion of the percutaneous access 404 device is reconnected and the mechanical auxiliary ventricle system, or blood pump 400, resumes its inflation and deflation synchronously with the natural heart.

The mechanical auxiliary ventricle system is designed to provide left ventricular support by means of diastolic augmentation. It includes three components: a blood pump 400, a percutaneous access device 404, and a drive unit 406. The blood pump 400 is an avalvular, single chamber bladder attached to the wall of the descending thoracic aorta. The blood contacting surface is textured to encourage fibrin deposition and eventual pseudoneointima formation. The pump 400 is driven with filtered air through a percutaneous access device 404. Normal pumping volume is 45 to 60 cc. The percutaneous access device 404 is a disc-shaped device that functions as the pneumatic and electrical conduit between the implanted blood pump 400 and the external drive unit 406. It also forms a biological seal between the skin and the implant. To enhance long-term stability, autologous fibroblasts are cultured onto its exterior surface. A Dacron velour covered flange creates a mechanically stable attachment to the underlying tissue. There are two types of drive units 406 that can control the blood pump 400. The line power drive unit, capable of continuous operation and a portable unit called the wearable drive unit. The wearable drive unit was designed to allow patient mobility while being pumped for up to one hour on batteries 408. Either unit may be used in a hospital or home environment.

The Blood Pump

The blood pump 400 is an avalvular, pneumatically actuated, unilayer, ellipsoidal bladder, approximately 165 millimeters (mm) long and 35 millimeters (mm) wide and weighing approximately 21 grams. It has a stroke volume of up to 60 cubic centimeters ($cm^3$ or cc). It was designed to have a geometry which significantly increases its life expectancy. The blood pump 400 uses a single layer of polyurethane which incorporates an integrally cast textured surface as the blood-device interface. This textured material is intended to foster formation of a pseudoneointima over the intravascular surface of the blood pump.

In order to limit the maximum stress to which the active wall of the bladder (pumping membrane) is exposed, the blood pump 400 has a molded back-plate. As the device is deflated, the pumping membrane conforms to the internal surface of the back-plate. The shape of the back-plate thus determines the maximum bending (strain) of the membrane. The back-plates are designed to minimize the strain.

The implantable blood pump 400 is a permanent, counterpulsating, auxiliary ventricle, based on intra-aortic balloon pump principles. It is implanted in the descending thoracic aorta. It is expected that the thoracic aorta location will minimize the risk of thromboembolic events. As in the intra-aortic balloon pump, flexible tubing connects the inflatable bladder to a console. The console provides the gas pressure required to inflate the bladder and control the timing and duration of inflation.

Preferably, the blood pump 400 is not exposed to a transmembrane pressure greater than 80 millimeters of mercury (mm Hg) during inflation, and preferably, full deflation of the blood pump 400 is achieved at the end of each deflation (less than 5 cc residual volume). It is preferable that the drive unit 406 operate to minimize the stress on the blood pump membrane to maximize its life expectancy, and that the drive unit 406 operate the blood pump 400 in such a way that it minimizes the workload of the heart.

For the system to deliver effective heart assistance in the form of counterpulsation, it must fully inflate the blood pump 400 and thereby maximally increase blood pressure during cardiac diastole and, just before ventricular systole, deflate the blood pump 400 fully, reducing blood pressure during systole and consequently unloading the natural heart.

Both drive units 406 meet these requirements when the diastolic pressure and heart rate are at the low to normal end of their range. When both heart rate and diastolic pressure are high, less than full stroke volume is achieved. While less than full stroke volume reduces the effectiveness of the pump 400, it does not compromise the safety of the pump 400. Stroke volume of the pump can be augmented by raising the power supply voltage to increase the maximum motor M speed and, and in turn, compressor 410 output. In other words, stroke volume of the pump can be augmented by increasing the pressure within the pressure reservoir 412 to achieve the desired stroke volume when both heart rate and diastolic pressure are high.

The Percutaneous Access Device

The percutaneous access device 404 consists of two components: an implanted component which serves as the terminus for the internal drive-line 402 to the blood pump 400 and for the electrocardiogram (ECG) leads 414 anchored in the vicinity of the left ventricle, and an external component, which serves as the terminus for the external drive-line from the drive unit 406 and mates the implanted component, allowing passage of gas and electrical signals.

The pneumatic connection to the mechanical auxiliary ventricle system is accomplished by a kink-resistant tube (internal drive-line) 402 that couples the percutaneous access device 404 to the blood pump 400. The inside diameter of the internal drive-line 402 is approximately 5 millimeters (mm), allowing rapid inflation and deflation. The internal drive-line 402 was designed to facilitate surgical implantation, and if necessary enable replacement of the percutaneous access device 404 without requiring thoracotomy.

The patient's electrocardiogram is sensed using a standard pacing lead 414. The electrodes are placed near the left ventricle to maximize ECG signal amplitude. An integral part of the interconnection is a pair of current limiters in the percutaneous access device (PAD) 404 that protect the patient from micro-shock hazards. These devices are similar to commercially available patient protection circuits with the exception of the extremely small size. Both alternating current (ac) and direct current (dc) are limited to less than 10 micro-amperes ($\mu$ Amps).

The ECG input circuitry has several functional blocks that are designed to protect the patient against leakage current and protect the drive unit from over-voltages. The first stage consists of a current limiter, similar in design to the one found in the percutaneous access device 404. It protects the patient from micro-shock hazards caused by equipment failures. An over-voltage protection block reduces the current and voltage that may be applied to other drive unit 406 electronic circuitry.

The implanted and external connection portions of the PAD 404 connection are held together by spring-loaded "fingers" mounted on the external half which grasp the ball on the surface of the internal half. If excessive force is applied, the connector halves release readily without damage to the patient or the connector.

The Drive Unit

The function of the drive unit 406 is to operate the blood pump 400, to detect impending system malfunction and to minimize untoward consequences to the patient. Pump 400 operation is controlled by a hybrid hardware/software subsystem that uses both ECG and blood pressure information. The ECG signal is used to determine the electrical event that defines the beginning of the cardiac cycle; the pressure information is used to extract the patient's systolic time intervals. This information is used to activate the pneumatic subsystem which provides diastolic augmentation by inflating the blood pump 400 during ventricular diastole and deflating just prior to ventricular systole. For its operation, the system also accepts information unique to an individual patient that can be entered manually by the attending physician.

The electronic system 18 is also used to detect impending malfunctions by performing diagnostic tests on the system. These include tests of the calibration of the pressure sensing components, integrity of the data acquisition system, and proper functioning of the compressor and pneumatic valves. Safety features built into the drive unit 406 are designed to protect the patient in the event of system failure, as well as to protect the integrity of the system. Protection is achieved by a number of hardware components, by continuous self-monitoring of the system operation and by built-in redundancy in the most critical elements of the system. Safety features include protection against current leakage, defibrillating voltages, failure of the microprocessor 24 and power supply 408 and over-inflation of the blood pump 400.

There are two basic drive units 406 available for activating the mechanical auxiliary ventricular system. One is a battery powered "wearable" drive unit, and the other is a line-powered drive unit capable of continuous operation.

The battery-powered, wearable drive unit was designed to be a portable, battery operated drive unit 406 of minimum size and weight. The battery pack 408 was chosen as a trade-off between weight and operation time. One hour was chosen as the nominal operating time on batteries, given charge density limitations of current battery technologies. As new battery technology becomes available, it is anticipated that the operation time will increase without sacrificing size and weight.

Standard line voltage provides a continuous source of power for the line-powered drive unit. This drive unit also includes a battery back-up system to maintain operation in the event of main power interruptions. The system can operate on the battery back-up for up to six hours.

The primary function of the drive unit 406 is to inflate and deflate the blood pump 400 synchronously with the patient's ECG, thereby providing diastolic augmentation. A simplified block diaphragm of the drive unit is presented in FIG. 4. The following is a description of the major features of the drive unit 406. Signal conditioning is achieved by feeding the ECG signal into analog signal conditioning circuitry 416. The circuitry 416 attenuates background noise and muscle noise by using appropriate filters and amplifiers. The conditioned signal then passes through means 418 for digitizing the signal. A program stored in memory of the control means 18 continuously monitors the signal and calculates two thresholds, one for amplitude and one for rise time. R-wave detection is accomplished by the program when both thresholds are exceeded within a given time period. In order to measure the patient's systolic time intervals, the drive unit 406 injects a small measured volume of gas into the mechanical auxiliary ventricle system. This forces the pumping membrane away from the backing plate of the blood pump 400, leaving the membrane flaccid. Thus the pressure within the blood pump 400 reflects the pressure in the aorta. This state is maintained preferably for at least two heartbeats. The program uses this information to adjust the inflation timing based on the systolic time interval. This method of measuring and processing the aortic pressure is referred to as a "partial cycle", or "scheduled pressure measurement", since the blood pump 400 is not fully inflated. This provides an aortic pressure measurement external of the patient using only the implanted blood pump 400. The blood pump 400 inflation/deflation timing is adjusted using the R-wave as the trigger and the data from the aortic pressure measurement. This value is based on the systolic timing interval and on physician selected parameters, referred to as the patient parameter table. The patient parameter table is specific to a particular patient, and can be reprogrammed as needed to maximize patient benefit.

Deflation timing is normally at the ECG trigger point. However, the physician may choose to delay deflation. The desired effect is to increase the length of the diastolic augmentation interval, and to reduce the possibility of drawing blood away from the coronary arteries by premature blood pump evacuation.

In order to perform the aortic pressure measurement and update pump timing, the partial cycle must be repeated to obtain current systolic time intervals. Timing is updated with changing patient conditions (as reflected by a change in the heart rate) or at scheduled time intervals. The physician can select the fixed time interval and program this into the patient parameter table.

The volume of gas delivered to the mechanical auxiliary ventricle system is measured and controlled on a beat-to-beat basis. This is accomplished by integrating the gas flow during the inflation period as depicted in the graph of FIG. 2 and the flow diagram of FIG. 3. Flow is sensed via means 16 for differential pressure measurement, such as pressure sensors 20 and 22, across the valve means 14. After adequate volume is delivered to the mechanical auxiliary ventricle system, the valve means 14 is closed. This volume is programmable through the patient parameter table. The desired volume is a trade-off between higher augmentation levels and membrane life. The system is preferably operated to maximize membrane life.

In order to be able to inflate the blood pump 400 at the desired speed, the pressure in the reservoir 412 must be maintained in an appropriate increment above the patient's aortic pressure. The program monitors the time required to fully inflate the blood pump 400 and adjusts the pressure in the reservoir 412 to achieve the desired inflation time, or as close to the desired time as possible within the mechanical limitations of the equipment. The desired speed of inflation (nominally 100 milliseconds (msec)) can be reprogrammed by the patient's physician.

The microprocessor 24 has a built-in timer that causes a reset if an internal register is not serviced within a given period of time. This function is referred to as a watch dog timer 420. It is designed to regain control of a processor 24 in case of a software execution error. The error can result from a programming fault, static discharge or noise on the computer bus, or other undefined malfunctions.

A secondary watchdog timer circuit has been implemented external to the microprocessor 24. Its purpose is to shut-off the motor M and valves 14 in case of software failure. This cut-off is a form of redundant protection to ensure power is removed from the motor M, and the deflate valves 422 revert to their normal open state. In this configuration, all gas in the mechanical auxiliary ventricle system is evacuated to atmosphere.

The portable drive unit 406 contains another safety feature to guard against erratic operation caused by low battery 408 voltage. The voltage regulator system 424 monitors the battery voltage and, when voltage decreases below a threshold value, executes a safe power-down procedure placing the valves 13, 422 and motor M in a safe state and then shutting itself down.

Two parallel, normally open valves 422 (only one is depicted in FIG. 4 for illustrative purposes) are used to exhaust the mechanical auxiliary ventricle system. In the event that one valve 422 fails and remains closed, the second valve 422 (not shown) ensures that the mechanical auxiliary ventricle system is fully evacuated, preventing a situation in which the aorta may become partially occluded. A mechanically operated relief valve V is used to limit reservoir 412 pressure. During the power-up sequence, the drive unit 406 adjusts the pressure to test the relief valve V to ensure that it is operational.

Software safety checks can be grouped into two categories. The first are one-time checks on power-up and the second category involves continuous monitoring of critic parameters. The majority of one-time tests occur when the power is first turned on.

The patient ECG input is electrically isolated to minimize micro-shock hazards. This is in addition to the current limiting circuits in the percutaneous access device 404, thereby providing redundant protection. The drive unit 406 is also protected from high voltage pulses that may result from defibrillators or other high energy sources. A signal conditioning block 416 amplifies and filters the ECG signal and feeds it into a data acquisition system.

The pneumatic subsystem is controlled by a computer 426. It consists of a servo controlled motor M and compressor 410, a pressurized fluid reservoir 412, inflate and deflate valve means, 14 and 422 respectively, and a manifold or fluid conduit 12 to port the stored gas to the drive line. The compressor 410 charges the reservoir 412 according to the patient's heart rate and diastolic pressure only to a level sufficient to provide full inflation of the blood pump 400. A spring loaded pressure relief valve V ensures that peak reservoir 412 pressure stays within safe limits. This mechanical valve V is meant as a back-up. Normally, the computer 426 maintains pressure by controlling motor M speed. However, if the patient's heart rate drops dramatically, the pressure could rise, temporarily, to the bleed setting on the relief valve V. Also, the computer 426 continually reads the reservoir 412 pressure and shuts the system down in case the pressure exceeds the bleed setting.

The solenoid valves, 14 and 422, and manifold control the flow of gas in the system. Inflate valves 14 connect the reservoir 412 to the drive line 402. The computer 426 then monitors the gas flow and closes the valve 14 when inflation is complete, or after a fixed maximum delay. Deflate valves 422 release gas from the blood pump 400 to atmosphere during systole. Since the deflate valves 422 are of the normally open variety, loss of power or failure of the drive unit 406 electronics results in evacuation of the blood pump 400. Furthermore, dual deflate valves 422 are used to ensure that the blood pump 400 is evacuated even if a valve 14 is physically jammed.

Pressure sensors 20 and 22 monitor the fluid conduit 12 output, reservoir pressure 412, and pressure across the inflate valves 14. These signals are fed into the data acquisition system to be processed by the computer 426. This information is used for gas flow control, aortic pressure monitoring, and two types of error checking procedures. The first type is a self-test on start-up of the system. This checks that internal hardware and sensors are performing as specified. Secondly, there are running checks of drive line 12 and reservoir 412 pressure to ensure that the drive line 12 and reservoir pressure 412 are within safe, expected limits. The analog signals from all sensors are fed through a signal conditioning module 416 into an analog to digital converter 418. The computer 426 reads and processes the information. This conversion system operates at high speed and high data throughput to minimize processor 24 overhead. Multiple channels are scanned rapidly compared to the sample rate to reduce the time skew of sample data.

The control means 18 is an embedded controller optimized for real time signal processing and control applications. The pressure sensors 20, 22 and ECG input 414 are part of a closed loop control system for shuttling gas to/from the blood pump 400. A typical power-up sequence can include one or more of the steps as described hereinafter. After power is switched on, an initialization and self-test procedure is executed. Computer memory, processor operation, software integrity, safety control system, sensors, valves, and compressor output are checked. The initialization also places the valve in a safe state before pumping begins. The patient ECG is then sampled and the trigger information is calculated. This becomes the time base for subsequent event detection and valve timing. The blood pump 400 is partially filled with gas and allowed to settle. This settling equalizes pressures on either side of the membrane, which then acts as a pressure sensor. No pumping takes place for two heartbeats to allow wave-form analysis. Then pumping begins with up-to-date patient information. The detection of events can be steered or overridden by a physician if the patient has special needs. This information is stored in the patient parameter table in non-volatile memory. Pumping continues with the defined parameters until another timing update is mandated. This is done at regular intervals, or if needed due to changing patient conditions. Pumping can be terminated by disconnecting the drive line, shutting the unit off, or running the batteries down to their end discharge point. Disconnection or low battery results in an error code that is meant to inform the user of actions required to continue pumping.

A microprocessor 24 monitor circuit senses computer activity and becomes active if program execution fails. In this event, the safety cutoff shuts down the motor M and valves 14, 422 regardless of computer state. The blood pump 400 is then placed in a safe state by evacuation to atmosphere. Pumping cannot be resumed. Unanticipated processor operation is considered to be an unrecoverable error. In this event, the processor shuts down. The drive unit 406 must be returned for maintenance.

Internal drive unit function can be monitored and modified through a high speed serial connection, either locally or remotely via modem. Patient wave-forms and drive unit status can be displayed on a standard personal computer running DOS. Under the direction of a physician, patient parameters that pertain to timing settings and error limits can be updated as appropriate for a particular patient. Also, the history of drive unit 406 function for a particular patient can be uploaded for analysis via the above described serial port. This history includes all error conditions encountered, unusual patient conditions, drive unit 406 and patient state at the time of the error, and run time of the unit. This data can be used to adjust the drive unit 406 to the patient, indicate the need for additional training of the patient in operation of the drive unit, demonstrate erroneous operation, and suggest maintenance when service intervals are exceeded.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for measuring flow rate and controlling delivered volume of fluid flow in a fluid conduit comprising:

valve means, disposed in said fluid conduit, for selectively opening and closing a fixed aperture between an open position and a closed position;

means for measuring a differential pressure between a first pressure on an upstream side of said valve means and a second pressure on a downstream side of said valve means; and means for accumulating said differential pressure with respect to time to provide a value corresponding to a volume of fluid flow passing through said valve means when in said open position.

2. The apparatus of claim 1 wherein said differential pressure measuring means further comprises:

first means for measuring said first pressure on said upstream side of said valve means and for generating a first signal corresponding to said first pressure;

second means for measuring said second pressure on said downstream side of said valve means and for generating a second signal corresponding to said second pressure; and means for determining said differential pressure from said first and second signals.

3. The apparatus of claim 1 wherein said differential pressure measuring means further comprises:

means for generating a signal corresponding to said differential pressure.

4. The apparatus of claim 1 further comprising:

means for comparing the value determined by the accumulating means to a target volume value;

when the value is at least as great as the target volume value, means for moving said valve means to said closed position prevents additional fluid flow through said aperture of said valve means; and when the target volume value is greater than the value, leaving said valve means in said open position to allow additional fluid flow through said aperture of said valve means.

5. The apparatus of claim 1 further comprising:

means for comparing the differential pressure to zero;

when the differential pressure is approximately equal to zero, means for moving said valve means to said closed position prevents additional fluid flow through said aperture of said valve means; and when the differential pressure is sufficiently greater than zero, leaving said valve means in said open position to allow additional fluid flow through said aperture of said valve means.

6. The apparatus of claim 1 further comprising:

means for comparing the second pressure to a safety pressure limit value;

when the second pressure is at least as great as the safety pressure limit value, means for moving said valve means to said closed position prevents additional fluid flow through said aperture of said valve means; and when the safety pressure limit value is greater than the second pressure, leaving said valve means in said open position to allow additional fluid flow through said aperture of said valve means.

7. The apparatus of claim 1 further comprising:

means for measuring a flow duration time interval;

means for comparing the flow duration time interval to a flow duration safety limit value;

when the flow duration time interval is at least as great as the safety limit value, means for moving said valve means to said closed position prevents additional fluid flow through said aperture of said valve means; and when the safety limit value is greater than the flow duration time interval, leaving said valve means in said open position to allow additional fluid flow through said aperture of said valve means.

8. The apparatus of claim 1 further comprising:

means for measuring flow rate and controlling delivered volume of fluid flow through said fluid conduit, said measuring means including the steps of:

measuring a differential pressure between a first pressure on an upstream side of said valve means and a second pressure on a downstream side of said valve means; and accumulating said differential pressure with respect to time to obtain a value corresponding to a volume of fluid flow passing through said valve means when in said open position.

9. A method for measuring flow rate and controlling delivered volume of fluid flow through a fluid conduit comprising the steps of:

selectively opening and closing valve means having a fixed aperture disposed in said fluid conduit between an open position and a closed position;

measuring a differential pressure between a first pressure on an upstream side of said valve means and a second pressure on a downstream side of said valve means; and when said valve means is in said open position, accumulating said differential pressure with respect to time to obtain a value corresponding to volume of fluid flow passing through said valve means.

10. The method of claim 9 wherein said differential pressure measuring step further comprises the steps of:

measuring said first pressure on said upstream side of said valve means;

generating a first signal corresponding to said first pressure;

measuring said second pressure on said downstream side of said valve means;

generating a second signal corresponding to said second pressure; and determining said differential pressure from said first and second signals.

11. The method of claim 9 wherein said differential pressure measuring step further comprises the step of:

generating a signal corresponding to said differential pressure.

12. The method of claim 9 further comprising the steps of:

comparing the value determined in the accumulating step to a target volume value;

when the value is at least as great as the target volume value, moving said valve means to said closed position to prevent additional fluid flow through said aperture of said valve means; and when the target volume value is greater than the value, leaving said valve means in said open position to allow additional fluid flow through said aperture of said valve means.

13. The method of claim 9 further comprising the steps of:

comparing the differential pressure to zero;

when the differential pressure is approximately equal to zero, moving said valve means to said closed position to prevent additional fluid flow through said aperture of said valve means; and when the differential pressure is sufficiently greater than zero, leaving said valve means in said open position to allow additional fluid flow through said aperture of said valve means.

14. The method of claim 9 further comprising the steps of:

comparing the second pressure to a safety pressure limit value;

when the second pressure is at least as great as the safety pressure limit value, moving said valve means to said closed position to prevent additional fluid flow through said aperture of said valve means; and when the safety pressure limit value is greater than the second pressure, leaving said valve means in said open position to allow additional fluid flow through said aperture of said valve means.

15. The method of claim 9 further comprising the steps of:

measuring a flow duration time interval;

comparing the flow duration time interval to a flow duration safety limit value;

when the flow duration time interval is at least as great as the safety limit value, moving said valve means to said closed position to prevent additional fluid flow through said aperture of said valve means; and when the safety limit value is greater than the flow duration time interval, leaving said valve means in said open position to allow additional fluid flow through said aperture of said valve means.

16. An apparatus for measuring flow rate and controlling delivered volume of fluid flow in a fluid conduit according to the method of claim 9 further comprising:

valve means, having a fixed aperture disposed in said fluid conduit, for selectively opening and closing said aperture between an open position and a closed position;

means for measuring a differential pressure between a first pressure on an upstream side of said valve means and a second pressure on a downstream side of said valve means; and means for accumulating said differential pressure with respect to time to provide a value corresponding to volume of fluid flow passing through said valve means when in said open position.

* * * * *